(12) United States Patent
Lu et al.

(10) Patent No.: US 8,849,727 B2
(45) Date of Patent: Sep. 30, 2014

(54) METHOD AND SYSTEM FOR CLASSIFYING BRAIN SIGNALS IN A BCI USING A SUBJECT-SPECIFIC MODEL

(75) Inventors: Shijian Lu, Singapore (SG); Cuntai Guan, Singapore (SG); Haihong Zhang, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 371 days.

(21) Appl. No.: 12/994,691

(22) PCT Filed: May 26, 2008

(86) PCT No.: PCT/SG2008/000192
§ 371 (c)(1),
(2), (4) Date: Nov. 24, 2010

(87) PCT Pub. No.: WO2009/145725
PCT Pub. Date: Dec. 3, 2009

(65) Prior Publication Data
US 2011/0289030 A1 Nov. 24, 2011

(51) Int. Cl.
*G06F 15/18* (2006.01)
*G06F 19/00* (2011.01)

(52) U.S. Cl.
CPC ........ *G06F 19/3443* (2013.01); *G06F 19/3437* (2013.01)
USPC .......................................................... 706/12

(58) Field of Classification Search
CPC ................................................. G06F 19/3443
USPC .................................................. 706/12, 20, 45
See application file for complete search history.

(56) References Cited

U.S. PATENT DOCUMENTS

2005/0017870 A1  1/2005  Allison et al.
2005/0085744 A1  4/2005  Beverina et al.

OTHER PUBLICATIONS

Blankertz et al., THe non-invasive Berlin Brain-Computer Interface: Fast Acquistion of Effective Performance in Untrained Subjects, 2007, Epub, pp. 1-12.*
Tagermann, Feature Selection for Brain-Computer Interfaces, 2007, pp. 1-10.*
Buttfield et al., Towards a Robust BCI: Error Potentials and Online Learning, 2006, IEEE, pp. 1-5.*
C. Guan, X. Zhu, M. Thulasidas, S. Ranganatha,and J. Wu, Robust classification of event-related potential for brain-computer interface, Int. Conf. Adv. Medical Signal Info Processing, pp. 321-326, 2004.
D.J. Krusienski, E. W. Sellers, F. Cabestaing, S. Bayoudh, D. J. McFarland, T.M. Vaughan, J.R. Wolpaw, "A comparison of classification techniques for the P300 Speller," Journal of neural engineering, vol. 3, No. 34, pp. 299-305, 2006.
E.A. Curran and M. J. Strokes, Learning to control brain activity: A review of the production and control of EEG components for driving brain-computer interface (BCI) systems, Brain and Cognition, vol. 51, pp. 326-336, 2003.

(Continued)

*Primary Examiner* — David Vincent
(74) *Attorney, Agent, or Firm* — Christie, Parker & Hale, LLP

(57) ABSTRACT

A method or system for classifying brain signals in a BCI. The system comprises a model building unit for building a subject-independent model using labelled brain signals from a pool of subjects.

25 Claims, 9 Drawing Sheets

(56) References Cited

OTHER PUBLICATIONS

J.R. Wolpaw, N. Birbaumer, D. J. McFarland, G. Pfurtscheiller, and T. M. Vaughan, Brain-computer interfaces for communication and control, Clinical Neurophysiology, vol. 113, pp. 767-791, 2002.

L. A. Farwell and E. Donchin, Talking off the top of your head: toward a mental prosthesis utilizing event-related brain potentials, Electroencephalography and Clinical Neurophysiology, vol. 70, pp. 510-523, 1988.

M. Thulandes, C. Guan, and J. Wu, Robust classification of EEG signal for brain-computer interface, IEEE Transactions on Neural Systems and Rehabilitation Engineering, vol. 14, No. 1, pp. 24-29, 2006.

Y. Li, H. Li, C. Guan and Z. Chin, A self-training semi-supervised support vector machine algorithm and its applications in brain computer interface, IEEE International Conference on Acoustics, Speech and Signal Pro., pp. 385-388, 2007.

* cited by examiner

100

METHOD AND SYSTEM FOR CLASSIFYING BRAIN SIGNALS IN A BCI USING A SUBJECT-SPECIFIC MODEL

CROSS-REFERENCE TO RELATED APPLICATION

This application is a National Phase Patent Application of and claims priority to International Application Number PCT/SG2008/000192, filed on May 26, 2008.

FIELD OF INVENTION

The present invention relates broadly to a method and system for classifying brain signals in a BCI system, and to a data storage medium having stored thereon computer code means for instructing a computer system to execute a method for classifying brain signals in a BCI.

BACKGROUND

Brain computer interface (BCI) [J. R. Wolpaw, N. Birbaumer, D. J. McFarland, G. Pfurtscheller, and T. M. Vaughan, Brain-computer interfaces for communication and control, Clinical Neurophysiology, vol. 113, pp. 767-791, 2002.; E. A. Curran and M. J. Strokes, Learning to control brain activity: A review of the production and control of EEG components for driving brain-computer interface (BCI) systems, Brain and Cognition, vol. 51, pp. 326-336, 2003.] functions as a direct communication pathway between a human brain and an external device. As it directly uses the electrical signatures of the brain's activity for responding to external stimuli, it is particularly useful for paralyzed people who suffer from severe neuromuscular disorders and are hence unable to communicate through the normal neuromuscular pathway. The electroencephalogram (EEG) is one of the widely used techniques out of many existing brain signal measuring techniques due to its advantages such as its non-invasive nature and its low cost.

Farwell and Donchin [L. A. Farwell and E. Donchin, Talking off the top of your head: toward a mental prosthesis utilizing event-related brain potential, Electroencephalography and Clinical Neurophysiology, vol. 70, pp. 510-523, 1988.] first demonstrated the use of P300 for BCIs in a so-called oddball paradigm. P300 is an endogenous, positive polarity component of the evoke-related-potential (ERP) elicited in the brain in response to infrequent/oddball auditory, visual or somatosensory stimuli. In the oddball paradigm, the computer displays a matrix of cells representing different letters, and flashes each row and column alternately in a random order. FIG. 1 shows an example of the matrix of cells 100 displayed by a computer in the oddball paradigm. A user trying to input a letter is required to pay attention to the target letter for a short while. In this process, when the row or column containing the intended letter flashes, a P300 will be elicited in the subject's EEG, which is then identified by using signal processing and machine learning algorithms.

One problem with using the P300 in BCIs is that large inter-subject variations exist among P300 of different subjects. For example, the P300 amplitude and latency vary among both normal and clinical populations. Such variations have been linked with individual differences in cognitive capability. Therefore, from the pattern recognition viewpoint, computational P300 classification models built for one subject does not accurately apply to another subject. To solve this problem, most P300-based BCIs usually first perform a special training session to learn a subject-specific classification model. In that special training session, a subject is required to follow instructions and focus on a particular cell visually at a given time while his or her EEG is being recorded. Subsequently, certain computer algorithms are implemented to perform the signal analysis and to learn a subject-specific classification model based on the recorded EEG. One problem with the special training session described above is that it is normally complicated and tedious, making most P300-based BCIs user-unfriendly. Furthermore, the requirement for the special training sessions makes the practical implementation of P300-based BCIs difficult.

Hence, in view of the above, there exists a need for a method and system for classifying brain signals in a BCI which seek to address at least one of the above problems

SUMMARY

In accordance with a first aspect of the present invention there is provided a method for classifying brain signals in a BCI, the method comprising the step of building a subject-independent model using labelled brain signals from a pool of subjects.

The method may further comprise the step of building an initial subject-specific model based on a set of feature vectors extracted from unlabelled brain signals from a new subject, applying both the subject-independent model and the initial subject-specific model for classifying the unlabelled brain signals.

The method may further comprise the step of adapting the initial subject-specific model using one or more of a group consisting of subsequent segments of unlabelled brain signals from the new subject, the subject-independent model and the initial subject-specific model.

The adapting may be performed until the subject-specific model achieves a consistent confidence score and subsequently the adapted subject specific model is used to give the classification of the brain signals.

The step of building the subject-independent model using labelled brain signals from a pool of subjects may further comprise the steps of acquiring the labelled brain signals from the pool of subjects; preprocessing the acquired labelled brain signals; constructing a set of feature vectors with their corresponding labels from the preprocessed brain signals; and building the subject-independent model by finding a weight vector for a linear combination of each feature vector to maximize the posterior probability that a P300 is evoked or not evoked given a feature vector.

The step of building the initial subject-specific model may comprise the steps of acquiring the unlabelled brain signals from the new subject; segmenting the acquired unlabelled brain signals; preprocessing the acquired unlabelled brain signals; extracting a set of feature vectors from the preprocessed unlabelled brain signals; and classifying the first segment of the unlabelled brain signals using the subject-independent model to build the initial subject-specific model.

The step of acquiring the labelled brain signals from the pool of subjects may further comprise the steps of providing a pre-defined set of stimuli in rows and columns; repeatedly activating the stimuli in rounds, wherein in each round, each row or column of stimuli is activated once; acquiring brain signals from the pool of subjects with each subject focused on a known stimulus; and labelling the acquired brain signals from the pool of subjects using the label of the known stimulus to give the labelled brain signals.

The step of acquiring the unlabelled brain signals from the new subject may further comprise the steps of providing a pre-defined set of stimuli in rows and columns; repeatedly activating the stimuli in rounds, wherein in each round, each row or column of stimuli is activated once; and acquiring the unlabelled brain signals from the new subject with the subject focused on an unknown stimulus.

The step of preprocessing the acquired labelled brain signals may further comprise the steps of implementing a low-pass filtering of the acquired labelled brain signals using an optimal cutoff frequency; down-sampling the filtered brain signals by averaging every five consecutive samples to a single sample; and removing ocular artifacts from the down-sampled brain signals.

The step of segmenting the acquired unlabelled brain signals may further comprise the step of including brain signals collected for more than one stimulus in the first segment and including brain signals collected for one stimulus in each of the subsequent segments.

The step of adapting the initial subject-specific model using one or more of a group consisting of subsequent segments of unlabelled brain signals from the new subject, the subject-independent model and the initial subject-specific model may further comprise the steps of iteratively a) classifying the feature vectors corresponding to the subsequent segment of the unlabelled brain signals using the subject-independent model; b) classifying the feature vectors corresponding to the subsequent segment of the unlabelled brain signals using the initial subject-specific model; c) evaluating a confidence score for the subject-independent model; d) evaluating a confidence score for the initial subject-specific model; e) classifying the feature vector corresponding to the subsequent segment of the unlabelled brain signals using the model with a higher confidence score; f) determining if the initial subject-specific model has achieved a consistent confidence score; g) adapting the initial subject-specific model using classification results from the model with a higher confidence score if the subject-specific model has not achieved a consistent confidence score; and repeating steps a) to g) with the adapted initial subject-specific model as the initial subject-specific model.

The step of evaluating the confidence score for the subject-independent model may further comprise the steps of evaluating a posterior probability that a P300 is evoked given the feature vector for each row of stimuli; evaluating a posterior probability that a P300 is evoked given the feature vector for each column of stimuli; determining the difference between the highest posterior probability among the rows of stimuli and the next highest posterior probability among the rows of stimuli to give a saliency of the highest posterior probability and multiplying said saliency to said difference; determining the difference between the highest posterior probability among the columns of stimuli and the next highest posterior probability among the columns of stimuli to give a saliency of the highest posterior probability and multiplying said saliency to said difference; combining the product of the saliency and the difference for the rows of stimuli and the columns of stimuli to evaluate a confidence score for the subject-independent model.

The step of evaluating the confidence score for the initial subject-specific model may further comprise the steps of evaluating a posterior probability that a P300 is evoked given the feature vector for each row of stimuli; evaluating a posterior probability that a P300 is evoked given the feature vector for each column of stimuli; determining the difference between the highest posterior probability among the rows of stimuli and the next highest posterior probability among the rows of stimuli to give a saliency of the highest posterior probability and multiplying said saliency to said difference; determining the difference between the highest posterior probability among the columns of stimuli and the next highest posterior probability among the columns of stimuli to give a saliency of the highest posterior probability and multiplying said saliency to said difference; combining the product of the saliency and the difference for the rows of stimuli and the columns of stimuli to evaluate a confidence score for the initial subject-specific model.

The step of determining if the initial subject-specific model has achieved a consistent confidence score may further comprise the steps of determining if the confidence score of the initial subject-specific model for a current segment of brain signals from the new subject is greater than a first threshold; determining if the standard deviation of the confidence scores of the initial subject-specific model for the last k segments of brain signals from the new subject is less than a second threshold; and determining that the initial subject-specific model has achieved a consistent confidence score if the confidence score of the initial subject-specific model for a current segment of brain signals is greater than said first threshold and the standard deviation of the confidence scores of the initial subject-specific model for the last k segments of brain signals is less than said second threshold.

The method may further comprise the step of identifying the unknown stimulus by identifying the row and the column in which the unknown stimulus lies wherein the stimulus in said row and said column results in a maximum averaged posterior probability that P300 is evoked given a feature vector.

In accordance with a second aspect of the present invention there is provided a system for classifying brain signals in a BCI, the system comprising a model building unit for building a subject-independent model using labelled brain signals from a pool of subjects.

The system may further comprise a second model building unit for building an initial subject-specific model based on a set of feature vectors extracted from unlabelled brain signals from a new subject, applying both the subject-independent model and the initial subject-specific model for classifying the unlabelled brain signals.

The system may further comprise a model adapting unit for adapting the initial subject-specific model using one or more of a group consisting of subsequent segments of unlabelled brain signals from the new subject, the subject-independent model and the initial subject-specific model.

The adapting may be performed until the subject-specific model achieves a consistent confidence score and subsequently the adapted subject specific model is used to give the classification of the brain signals.

The system may further, comprise a stimulation unit comprising a set of stimuli in rows and columns; wherein the stimulation unit repeatedly activates the stimuli in rounds, such that in each round, each row or column of stimuli is activated once; an acquisition unit for acquiring brain signals; and a preprocessing unit for preprocessing the acquired brain signals.

In accordance with a third aspect of the present invention there is provided a data storage medium having stored thereon computer code means for instructing a computer system to execute a method for classifying brain signals in a BCI, the method comprising the step of building a subject-independent model using labelled brain signals from a pool of subjects.

The method may further comprise the step of building an initial subject-specific model based on a set of feature vectors extracted from unlabelled brain signals from a new subject, applying both the subject-independent model and the initial subject-specific model for classifying the unlabelled brain signals.

The method may further comprise the step of adapting the initial subject-specific model using one or more of a group consisting of subsequent segments of unlabelled brain signals from the new subject, the subject-independent model and the initial subject-specific model.

The adapting may be performed until the subject-specific model achieves a consistent confidence score and subsequently the adapted subject specific model is used to give the classification of the brain signals.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
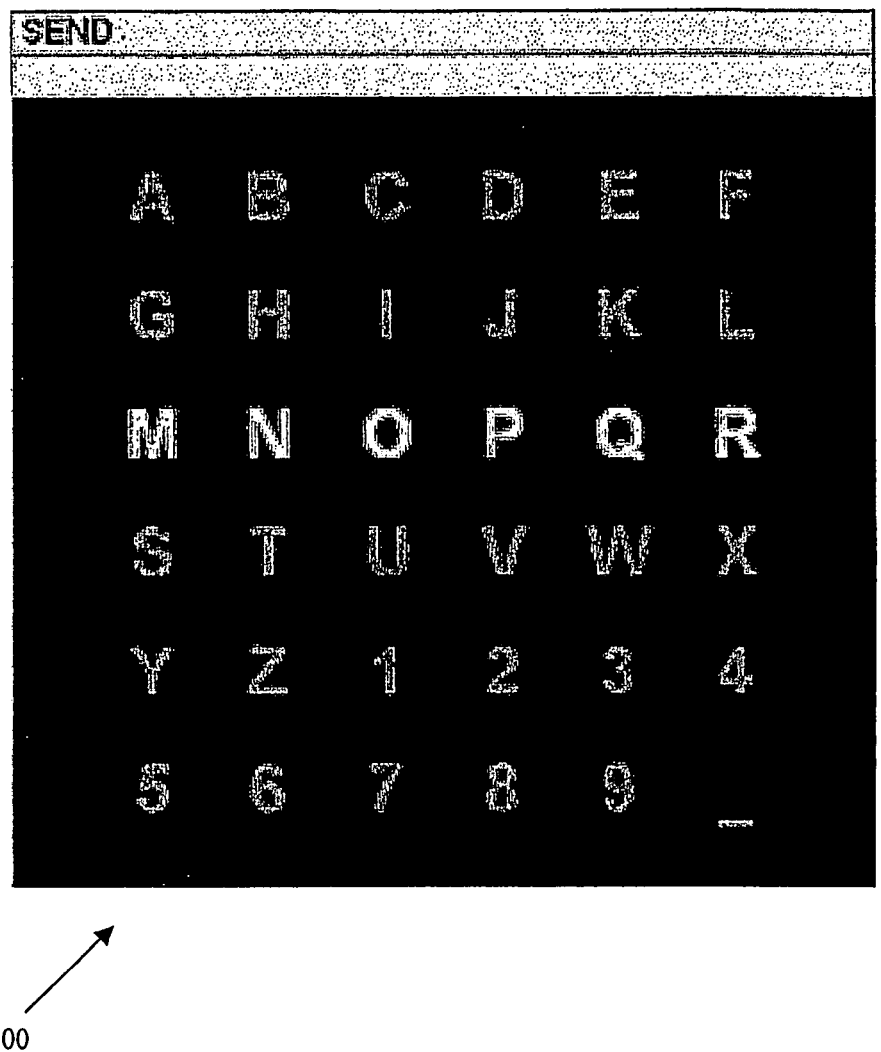
FIG. 1 shows an example of a matrix of cells displayed by a computer in an oddball paradigm.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "calculating", "generating", "building", "adapting", "acquiring", "preprocessing", "constructing", "segmenting", "classifying", "providing", "activating", "labelling", "implementing", "down-sampling", "removing", "predicting", "evaluating", "determining", "combining", "identifying" or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

Embodiments of the present invention employ a zero-trained subject EEG modeling and classification technique to address the above-mentioned problems. The inventors have recognized that despite the existence of large inter-subject variations within the P300 of different subjects, there remain common characteristics within the P300 of different subjects. One example of such a common characteristic is the positive peak in the P300 after 300 ms from the time an external stimulus is applied. Compared with a P300 model learned from one specific subject, a P300 model learned from a pool of subjects can be more capable in capturing the common characteristics. Such a subject model learned from a pool of subjects in the example embodiments can be referred to as the subject-independent model (SIM) because it is independent of any specific subject and can capture the common P300 characteristics. Such a SIM can identify the P300 of a new subject without special training and hence has a higher potential in classifying EEG of people in general without the special training.

Although the SIM in the example embodiments is capable of identifying P300 of a new subject without special training, the identification accuracy may be lower than that of a supervised subject specific model (SSM) learned from a subject's labelled EEG. This can be attributed to the fact that the SIM captures the common P300 characteristics instead of the subject-specific P300 characteristics.

The example embodiments can additionally make use of the EEG of a new subject and accordingly capture the subject-specific P300 characteristics through an unsupervised learning process. Such example embodiments include a new P300 modeling and identification technique that adapts a SIM to a SSM through an unsupervised learning process. Given labelled EEG of a pool of subjects and unlabelled EEG of a new subject, the EEG of the new subject is initially classified by using a SIM. A SSM is then built based on the initially classified EEG segment of the new subject and the corresponding labels predicted by the SIM. Subsequently, both the SIM and the newly built SSM are deployed to classify the ensuing subject EEG. The classification results can then be determined according to the model with the higher confidence score. In this way, the SSM can be iteratively updated by incorporating the newly classified subject EEG which is dependent on the ensuing EEG of the new subject and the corresponding labels predicted by either the SIM or the SSM, depending on their classification confidence score. This adaptation process can be terminated in such embodiments when the adapted SSM has achieved consistency.

In the example embodiments, collection of the EEG from the subjects using a P300-based word speller system is performed. Further details of the P300-based word speller system can be found in [T. Manoj, C. Guan, and W. Jiankang. Robust classification of EEG signal for brain-computer interface, IEEE Transactions on Neural Systems and Rehabilitation Engineering, vol. 14, no. 1, pp. 24-29, 2006.], details of which are incorporated herein by cross-reference.

During the collection of the EEG in the example embodiments, subjects are equipped with an electro-cap that has 64 electrodes mounted. The EEG collected from the subjects is first amplified by for example, a Neuroscan amplifier called SynAmps2 and then piped to a server by for example, the Neuroscan software. The SynAmpls2 has 64 mono-polar channels through which the measured EEG is transmitted. In one example, 24 out of the 64 channels are automatically selected and the EEG sampling rate is set at 250 Hz.

Furthermore, during the EEG collection stage in the example embodiments, subjects sit in front of a 6×6 matrix of cells with each cell displaying a character as shown in FIG. 1 and the six rows and columns flash successively and randomly. Subjects are required to focus on one specific cell during a flashing round whereby each round is defined by the flashing of each row or column once. When a particular row or column flashes, a corresponding stimulus code is generated in a time-locked fashion and divides the collected EEG into epochs of 500 ms starting from the time the stimulus appears. The focused cell corresponding to one row flash and one column flash within each round can be determined through the identification of the P300 within the epoched EEG.

Figure 2:
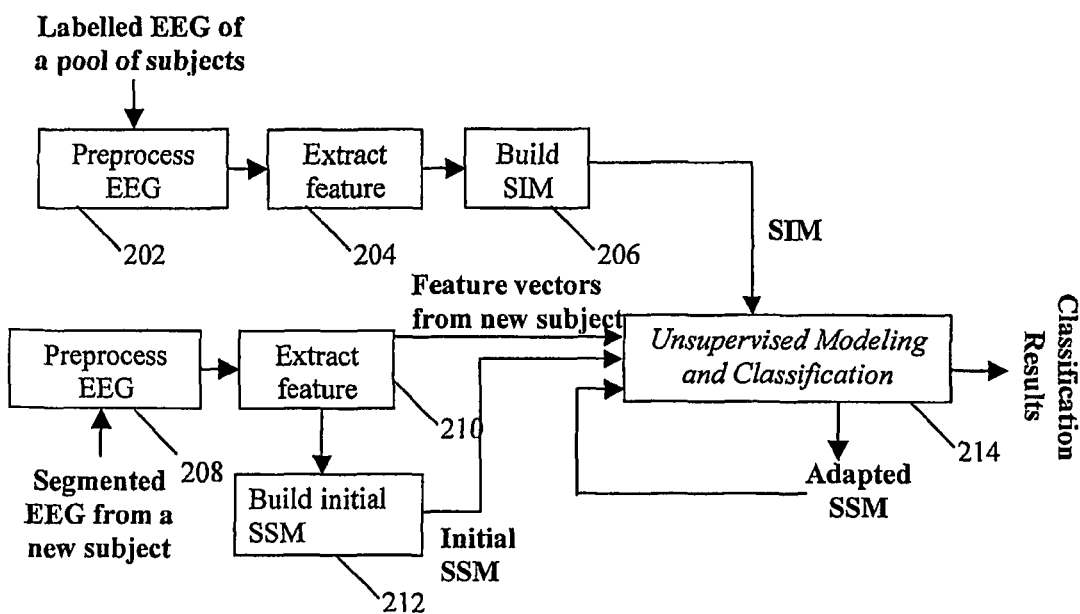
FIG. 2 shows a flowchart illustrating a zero-trained P300 identification technique according to an embodiment of the present invention.

FIG. 2 shows a flowchart illustrating a zero-trained P300 identification technique 200 according to an embodiment of the present invention. The input to the technique 200 in FIG. 2 is a set of labelled EEG, E, collected from a pool of subjects and unlabelled EEG, E', collected, from a new subject. The collection process has been described above.

In step 202, the labelled EEG from a pool of subjects, E, is preprocessed. In one example, the EEG is preprocessed by first implementing a low-pass filtering of the EEG using an optimal cutoff frequency [C. Guan, X. Zhu, S. Ranganatha, M. Thulasidas, and J. Wu, Robust classification of event-related potential for brain-computer interface, Int. Conf. Adv. Medical Signal Info. Processing, pp. 321-326, 2004.]. The filtered EEG is then down-sampled for example, by averaging every five consecutive EEG samples to a single EEG sample. Such down-sampling reduces the data size and at the same time speeds up the ensuing EEG processing significantly.

Ocular artifacts are then removed by treating the sampled EEG y(n) as a linear superposition of the measured EOG u(n) and the real EEG w(n) according to Equation (1). In Equation (1), N is the number of sites at which the EOG measurement is done. In one example, N is equal to two.

$$y(n) = \sum_{i=1}^{N} b_i u_i(n) + w_i(n) \quad (1)$$

In one example, the EOG is removed by using a difference model which removes the inter-sample correlations of the required EEG w(n) as shown in Equation (2). In Equation (2), n'=n−1. Since the dynamic range of w is small in comparison to u, the propagation constants $b_i$ can be computed through the least square minimization. Further details of the difference model can be found in T. Manoj, C. Guan, and W. Jiankang. Robust classification of EEG signal for brain-computer interface, IEEE Transactions on Neural Systems and Rehabilitation Engineering, vol. 14, no. 1, pp. 24-29, 2006, details of which are incorporated herein by cross-reference.

$$y(n) = y(n') + \sum_{i=1}^{N} b_i(u_i(n) - u_i(n')) + w_i(n) - w_i(n') \quad (2)$$

In step 204, feature extraction is performed such that the preprocessed EEG is converted into a set of feature vectors together with their corresponding labels. In step 206, a SIM is built based on the set of feature vectors together with their corresponding labels obtained in step 204. Further details of steps 204 and 206 are as follows.

In the example embodiment, a total of 12 flashes intensify in a random order within each round. In each round, the flashing of a particular row or column within which the focused cell lies results in a P300 evoked in the subject whereas the flashing of the remaining rows or columns does not result in any P300 being evoked in the subject. Therefore, the P300 identification can be treated as a two-class classification problem. To facilitate the P300 identification, the preprocessed EEG $E_{c \times s}$ collected within each trial is first converted into a feature vector as shown in Equation (3). In Equation (3), x(i) refers to the EEG collected from the i-th selected channel and the parameter c refers to the number of channels selected. In one example, the EEG collected from the i-th selected channel is composed of s EEG signals sampled between 150 ms and 500 ms after each flash and the number of channels selected is 24.

$$x = [x(1)^T, \ldots, x(i)^T, \ldots, x(c)^T]^T \quad (3)$$

In the example embodiment, it can be assumed that the EEG feature vector x (either with or without P300) has a multivariate Gaussian distribution with mean $\mu_i$ and covariance $\Sigma_i$ according to Equation (4). In Equation (4), x refers to the feature vector converted from $E_{c \times s}$ and p=c×s is equal to the dimension of the feature vector x. The parameter $\theta_b$ represents the hypothesis that the EEG contains P300 when i=1 and represents the hypothesis that the EEG does not contain P300 when i=2. $p(x|\theta_i)$ refers to the probability that the feature vector x is obtained given the hypothesis $\theta_i$. In addition, parameters $\mu_i$ and $\Sigma_i$, i=1, 2 refer to the mean and the covariance of the feature vector x with and without the presence of P300, respectively.

$$p(x \mid \theta_i) = \frac{1}{2\pi^{p/2}|\Sigma|^{1/2}} e^{-\frac{1}{2}(x-\mu_i)^T \Sigma^{-1}(x-\mu_i)}, \; i = 1, 2 \qquad (4)$$

P300 is identified using Fisher's linear discriminant in the example embodiment. The Fisher's linear discriminant is chosen because of its lower computational cost and its superior performance as compared to other P300 identification techniques as reported in [D. J. Krusienski, E. W. Sellers, F. Cabestaing, S. Bayoudh, D. J. McFarland, T. M. Vaughan, J. R. Wolpaw, "A comparison of classification techniques for the P300 Speller," *Journal of neural engineering*, vol. 3, no. 34, pp. 299-305, 2006.]. However, other P300 identification techniques such as the Pearson's correlation method, stepwise linear discriminant analysis, and Support Vector Machine (SVM) can also be used.

The Fisher's linear discriminant in the example embodiment attempts to find a linear combination w that projects a high-dimensional feature x into a one-dimensional feature g(x) according to Equation (5). In Equation (5), w and $w_0$ refer to the weight vector and bias. For the two-class case, the linear discriminant $g_1(x)=g_2(x)$ defines a boundary surface, which is a hyperplane whose orientation is determined by the w in Equation (5).

$$g(x) = w^T x + w_0 \qquad (5)$$

The Fisher's linear discriminant in the example embodiment seeks to determine a linear combination of the feature vector x that maximizes the ratio of its between-classes variance to its within-classes variance according to Equation (6). In Equation (6), $S_b$ and $S_w$ correspond to the between-classes scatter matrix and within-classes scatter matrix, respectively whereas J(w) is the generalized Rayleight quotient. For the two-class case, the two scatter matrices in Equation (6) can be estimated from the training EEG according to Equation (7). In Equation (7), $\mu_1$ and $\mu_2$ refer to the mean of the EEG feature vectors with and without P300, respectively.

$$\underset{w}{\operatorname{argmax}} J(w) = \frac{w^T S_b w}{w^T S_w w} \qquad (6)$$

$$S_w = \sum_{i=1}^{2} \sum_{x \in D_i} (x-\mu_i)(x-\mu_i)^T, \qquad (7)$$

$$S_b = (\mu_1 - \mu_2)(\mu_1 - \mu_2)^T, \; i = 1, 2$$

The orientation of the boundary surface w (weight vector) that maximizes the quantity J(w) can be determined according to Equation (8). As the feature vector x is distributed normally, the weight vector w in Equation (8) can be similarly derived by the discriminant function that maximizes the posterior probability $g_i(x)$ according to Equation (9). In Equation (9), $p(\theta_i|x)$ refers to the posterior probability that given the hypothesis $\theta_i$, the feature vector x is obtained whereby $\theta_i$ represents the hypothesis that the EEG contains P300 when i=1 and represents the hypothesis that the EEG does not contain P300 when i=2. In short, $p(\theta_i|x)$ is the P300 and the non-P300 posterior probability of the feature vector x for i=1 and 2 respectively. Furthermore, $p(\theta_i)$ refers to a priori probability and in one example, $p(\theta_i)$ is equal to ⅙ and ⅚ for i=1 and 2 respectively. In addition, $p(x|\theta_i)$, i=1, 2 follows a multivariate Gaussian distribution according to Equation (4) and the parameters, $\mu$ and $\Sigma$, can be estimated from the feature vector x converted from the training EEG.

$$w = S_w^{-1}(\mu_1 - \mu_2) \qquad (8)$$

$$g_i(x) = \ln p(\theta_i|x) = \ln p(x|\theta_i) + \ln(p(\theta_i)), \; i=1,2 \qquad (9)$$

To build the SIM model, the pooled labelled subject EEG is converted into a set of feature vectors and the corresponding labels according to Equation (10). In Equation (10), $x_{si}$ and $l_{si}$ refer to the feature vector converted from EEG of the i-th subject and its corresponding labeling, respectively.

$$X = \{[x_{s1}^T, l_{s1}], \ldots, [x_{si}^T, l_{si}], \ldots, [x_{sn}^T, l_{sn}]\} \qquad (10)$$

With the pooled EEG X in Equation (10), the Gaussian distribution $p(x|\theta_i)$ ($\mu_i$ and covariance $\Sigma_i$) in Equation (9) can be estimated and a SIM can then be built based on Fisher's linear discriminant.

Unlabelled subject EEG, E', from a new subject is divided into a number of roughly equal segments i.e. segmented and is preprocessed in step 208. In one example, the preprocessing in step 208 is the same as that in step 202.

In step 210, feature extraction is performed whereby the segmented and preprocessed EEG is converted into a set of feature vectors. In one example, the set of feature vectors can be expressed in the form $X' = \{x_{s_i}, \ldots x_{s_i}, \ldots x_{s_n}\}$ where $x_{s_i}$ is the feature vector corresponding to the i-th EEG segment of the new subject.

In step 212, an initial SSM is built based on the feature vector $x_{s_i}$ corresponding to the first segment of the EEG of the new subject and its corresponding label $l_{s_i}$ whereby the corresponding label is predicted by classifying the feature vector $x_{s_i}$ using the SIM built in step 206. Therefore, the EEG of a new subject can be classified and the initial SSM can be built using the SIM without special training.

In step 214, unsupervised modeling and classification is performed to output an adapted SSM and to give the final classification results. In the example embodiments, except for the first EEG segment of the new subject whose labels are solely predicted by the SIM (i.e. during the building of the initial SSM), the ensuing EEG segments of the new subject are all classified by both the SIM and the SSM in step 214. One example of step 214 is illustrated in FIG. 3.

Figure 3:
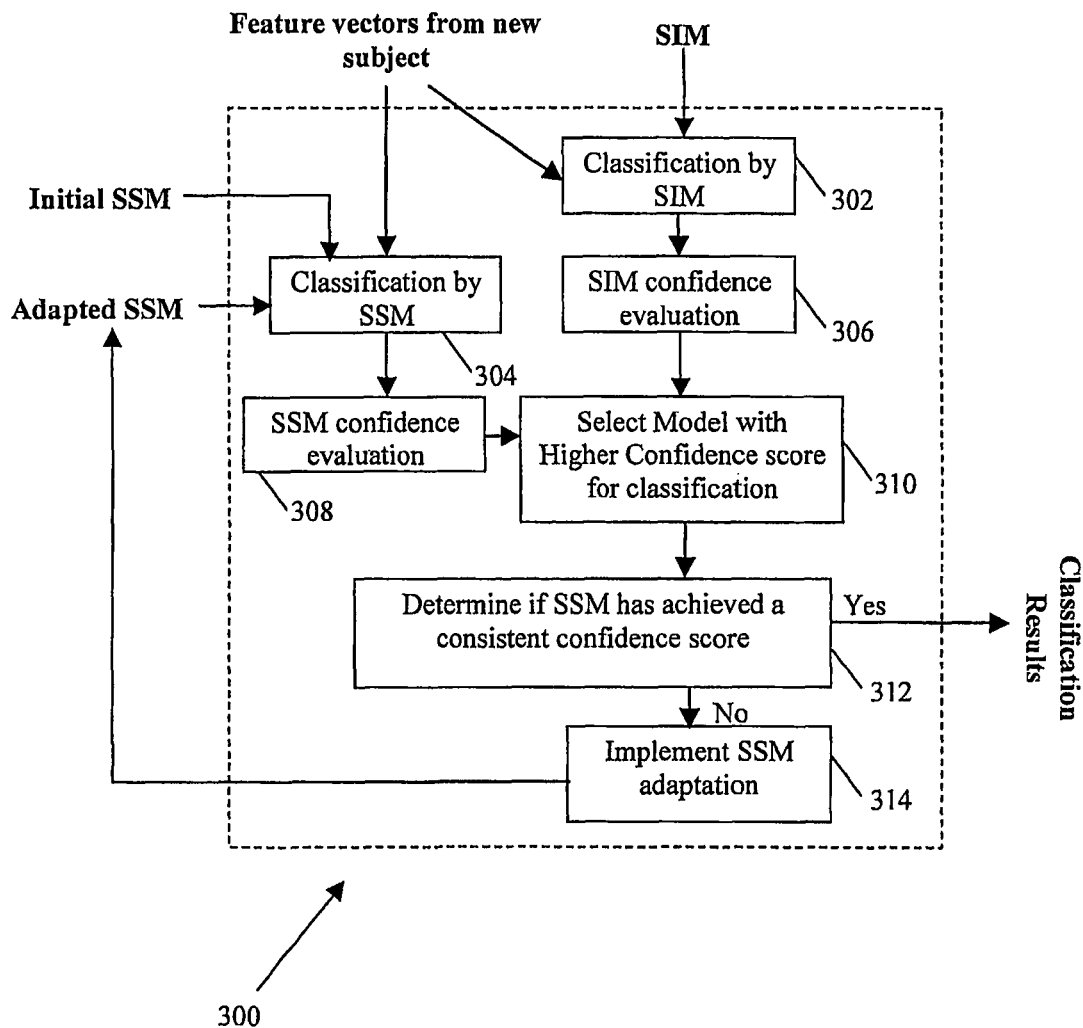
FIG. 3 shows a flowchart illustrating an unsupervised modeling and classification technique according to an embodiment of the present invention.

FIG. 3 shows a flowchart illustrating an unsupervised modeling and classification technique 300 according to an embodiment of the present invention. In step 302, the feature vector of the ensuing EEG segment of the new subject, $x_{s_i}$, is classified using the SIM whereas in step 304, the feature vector of the ensuing EEG segment of the new subject, $x_{s_i}$, is classified using the SSM.

In step 306, SIM confidence evaluation is performed whereas in step 308 SSM confidence evaluation is performed. Further details of steps 306 and 308 are as follows.

To facilitate the ensuing SSM adaptation, the P300 and non-P300 posterior probabilities of the feature vector x in Equation (9) i.e. $g_1$ and $g_2$ respectively, are transformed according to Equation (11). In Equation (11), $G=[g_1, g_2]$ corresponds to the posterior probability of there being a P300 and no P300 as evaluated by Equation (9). Thus the transformation in Equation (11) maps the posterior probability to a transformed posterior probability with a value between 0 and 1.

$$\phi_i \frac{e^{g_i - min(G)}}{\sum_{i=1}^{2} e^{g_i - min(G)}} \quad (11)$$

In steps 306 and 308, scores are defined to indicate the models' confidence in the P300 identification. In one example, the models' confidence scores are defined based on the transformed P300 posterior probability (as evaluated in Equation (11)) according to Equation (12). In Equation (12), $\phi_{1,rmax}$ and $\phi_{1,cmax}$ are the maximum P300 posterior probabilities among the flashing rows and columns respectively whereas $\phi'_{1,rmax}$ and $\phi'_{1,rmax}$ are the second maximum P300 posterior probabilities among the flashing rows and columns respectively. As shown in Equation (12), the confidence score is high when the maximum P300 posterior probability and the saliency of the maximum. P300 posterior probability (given by the difference between the maximum P300 posterior probability and second maximum P300 posterior probability) are both high.

$$conf = (\phi_{1,rmax} - \phi'_{1,rmax}) + (\phi_{1,cmax} - \phi'_{1,cmax}) \quad (12)$$

In step 310, the model with the higher confidence score is selected to classify $x_{s_i}$ for the i-th segment and the label of $x_{s_i}$ i.e. ($l_{s_i}$) is predicted by either the SIM or the SSM depending on which model has a higher confidence score. In one example, the labels of the ensuing EEG segments of the new subject are determined based on the confidence scores of the SIM and SSM according to Equation (13). In Equation (13), $conf_{SIM}$ and $conf_{SSM}$ refer to the confidence scores of the SIM and the SSM (as evaluated by Equation (13)), respectively and $l_{sim}$ and $l_{ssm}$ refer to the labels predicted by the SIM and SSM respectively.

$$l_{s_i} \begin{cases} l_{sim} & \text{if } conf_{SIM} \geq conf_{SSM} \\ l_{ssm} & \text{otherwise} \end{cases} \quad (13)$$

In step 312, it is determined if the SSM has achieved a consistent confidence score. If so, the final classification results are the classification results obtained in step 310. If it is determined in step 312 that the SSM has not achieved a consistent confidence score, SSM adaptation is performed in step 314. In step 314, the SSM is updated to give an adapted SSM using all the EEG segments, $x_{s_1}, \ldots, x_{s_i}$ classified so far and their corresponding labels determined in step 310.

In one example, the adaptation of the SSM in the example embodiment is terminated when the SSM has achieved a consistent confidence score according to Equation (14). If the conditions in Equation (14) are satisfied, it is determined that the SSM has achieved consistency. In Equation (14), $conf_{i,SSM}$ and $conf_{i-k,SSM}$ refer to the confidence scores of the just classified and the last k classified EEG segments of the new subject, respectively. Generally, the parameter k can be a number lying between 3 and 8. The number is set at 5 in this example implementation. Furthermore, parameters $T_1$ and $T_2$ refer to predetermined thresholds for the confidence score, $conf_{i,SSM}$ and the confidence consistency $S([conf_{i-k,SSM}, \ldots, conf_{i,SSM}])$ respectively. The function $S()$ evaluates the standard deviation of the input vector $[conf_{i-k,SSM}, \ldots, conf_{i,SSM}]$ whereby this input vector represents the confidence scores of multiple consecutive EEG segments.

$$\begin{cases} conf_{i,SSM} > T_1 \\ S([conf_{i-k,SSM}, \ldots, conf_{i,SSM}]) < T_2 \end{cases} \quad (14)$$

Steps 302 to 314 are repeated until it is determined in step 312 that the SSM has achieved a certain level of consistency and confidence. The output of FIG. 3 is hence an adapted SSM capable of classifying EEG of the new subject and the final classification results of the subject EEG given by this adapted SSM during the model adaptation.

In the example embodiment, multiple rounds of flashing are implemented for the subject to input one character and the focused cell is identified by the row flash and the column flash that resulted in the maximum averaged P300 posterior probability over multiple rounds of flashing (i.e. $row_{P300}$ and $col_{P300}$ respectively) according to Equation (15). In Equation (15), $\phi_{1,irow,j}$ and $\phi_{1,icol,j}$ are respectively the posterior probabilities that P300 is evoked during the irow-th and the icol-th flash within the j-th round of flashing. R is the number of rounds implemented and is equal to 10 in one example.

$$row_{P300} = \underset{irow}{\operatorname{argmax}} \sum_{irow=1}^{6} \sum_{j=1}^{R} \phi_{1,irow,j} \quad (15)$$

$$col_{P300} = \underset{icol}{\operatorname{argmax}} \sum_{icol=1}^{6} \sum_{j=1}^{R} \phi_{1,icol,j}$$

The advantages of the example embodiments include the following.

The technique in the example embodiment adapts a SIM to a SSM in an unsupervised manner and is superior to semi-supervised learning techniques [Y. Li, H. Li, C. Guan and Z. Chin, A self-training semi-supervised support vector and its applications in brain computer interface, IEEE International Conference on Acoustics, Speech and Signal Pro., pp. 385-388, 2007.], which are used when only a small amount of labelled data are available. In contrast to the semi-supervised learning techniques, the technique in the example embodiments requires no EEG labels of the new subject. Instead, it uses the SIM as a seed model to make an initial label prediction. Furthermore, the example embodiment includes a new P300 modeling and identification technique that adapts the subject-independent P300 model (i.e. SIM) to a SSM in an unsupervised manner.

To further illustrate the advantages of embodiments of the present invention, experimental results from the implementation of the example embodiment of the present invention are presented below.

In the experiment, the technique in the described example embodiment is tested over a P300-based word speller. Further details of the P300-based word speller can be found in [T. Manoj, C. Guan, and W. Jiankang. Robust classification of EEG signal for brain-computer interface, IEEE Transactions on Neural Systems and Rehabilitation Engineering, vol. 14, no. 1, pp. 24-29, 2006.], the contents of which are incorporated herein by cross-reference. In this speller system in the experiment; subjects are equipped with an electro-cap that has 64 electrodes. The subject EEG is first amplified by a Neuroscan amplifier called SynAmps2 and is then piped to a server by the Neuroscan software. 24 out of the 64 channels of the SynAmps2 are selected and the EEG sampling rate is set at 250 Hz [C. Guan, X. Zhu, S. Ranganatha, M. Thulasidas, and J. Wu, Robust classification of event-related potential for brain-computer interface, Int. Conf. Adv. Medical Signal Info. Processing, pp. 321-326, 2004.].

In the experiment, during the EEG collection stage, the subjects sit in front of a 6×6 matrix of cells with each cell displaying a character as shown in FIG. 1 where the six rows and columns flash successively and randomly. Subjects are required to focus on one specific cell visually during a flashing round. When a particular row or column flashes, a corresponding stimulus code is generated in a time-locked fashion, which divides the collected EEG into epochs of 500 ms starting from the time the stimulus appears. Therefore, the focused cell corresponding to one row flash and one column flash within each round can be identified through the identification of the P300 within the epoched EEG.

Furthermore, in the experiment, the EEG of ten healthy subjects is collected. For each subject, two EEG sessions are collected sequentially, which correspond to the input of the same set of 41 characters "THE QUICK BROWN FOX JUMPS OVER LAZY DOG 246138 579" in two different orders. In addition, ten rounds of flashes are implemented for each character. Within each round, the EEG between 150 ms and 500 ms following each flash are used for the P300 identification. These two sessions of EEG are used to evaluate the P300 identification technique in the experiment.

In one experiment, the P300 variability is studied. Tough P300 is commonly defined by a positive peak after 300 ms of elicited stimuli whereas the real P300 usually varies greatly from subject to subject in terms of its peak amplitude and its peak latency. Consequently, a P300 model learned from one subject usually cannot apply well to another subject.

In the experiment, the P300 variability is studied through the examination of the cross-subject EEG classification. First, ten subject models are built by learning from the first session of EEG (or the second session depending on the two-fold cross validation) of the ten healthy subjects. Subsequently, the ten subject models are then used to classify the second session of EEG (or the first session depending on the two-fold cross validation) of the ten healthy subjects.

Table 1 shows the cross-subject P300 identification accuracies. In particular, the rows in Table 1 represent the ten subject models and the columns represent the second (or the first) session of EEG of the ten healthy subjects to be classified. Therefore, the diagonal items in Table 1 show the subject-specific accuracies, which are evaluated by using the models learned from the subject's own EEG to classify the second (or first) session of EEG whereas the non-diagonal items give the cross-subject accuracies, which are evaluated by using the models that are learned from EEG of other subjects to classify the second (or first) session of EEG.

Figure 4:
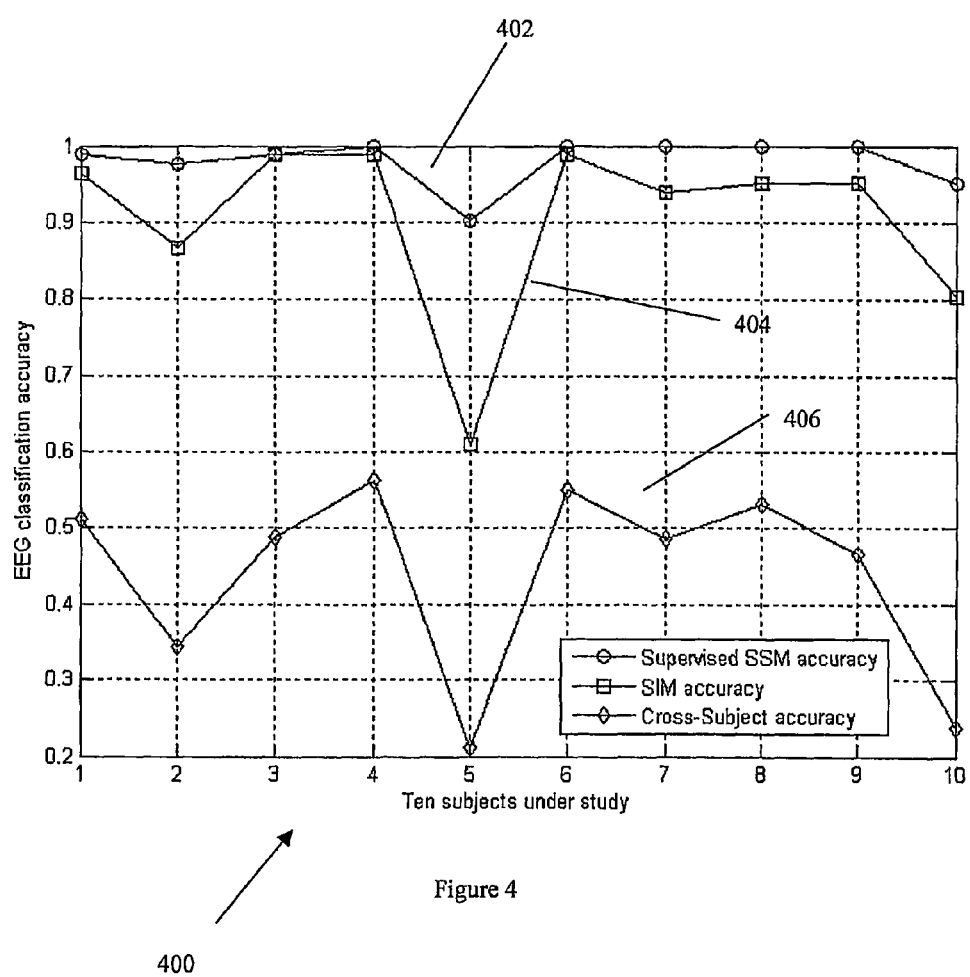
FIG. 4 shows a plot illustrating the performances of different P300 identification techniques.

In addition, FIG. 4 shows a plot 400 illustrating the performances of different P300 identification techniques. In FIG. 4, the graph 402 labelled by circles shows the accuracy of the subject-specific P300 models corresponding to the diagonal items in Table 1 and the graph 406 labelled by diamonds shows the cross-subject accuracy that is derived by averaging the non-diagonal items in Table I in each column.

From Table 1 and FIG. 4, it can be seen that the cross-subject accuracy as shown by graph 406 (non-diagonal items in Table 1) is significantly lower than the subject-specific accuracy as shown by graph 402 (diagonal items in Table 1), indicating the EEG variability among different subjects.

In FIG. 4, the subject-independent P300 identification technique i.e. SIM of an example embodiment is also tested. For each of the ten healthy subjects, a SIM is built by learning from the EEG of the other nine subjects according to Equation (16). In Equation (16), $TR_j$ refers to the first session of EEG (or the second session of EEG depending on two-fold cross-validation) of the j-th subject and $P_i$ refers to the EEG of the other nine subjects used to train a SIM of a subject under study. The trained SIM is then used to classify the second session of EEG (or the first session of EEG depending on two-fold cross-validation) of the i-th subject.

$$P_i = \{TR_j, \text{for } j=1 \ldots 10, \text{where } j \neq i\} \quad (16)$$

In FIG. 4, the graph 404 labelled by squares shows the accuracy of the SIM for each subject. As shown in graph 404, the accuracy of the SIMs is generally much higher than that of the cross-subject models. While the accuracy of the SIMs is still lower than that of the SSMs, the results indicate that the combination of EEG of a pool of subjects in this example embodiment advantageously augments the performance of the EEG classification greatly, compared to the use of cross-subject models.

In the experiment, to remove the possible effects of the EEG collection order, 41 characters in one session are randomly sorted and subsequently divided into 40 segments including 2 characters in the first segment and 1 in each of the remaining 39 segments. In addition, to get more comprehensive classification results, ten rounds of the random character sorting and segmenting described above are implemented for each of the two sessions, and the graphs shown in FIG. 4 relate to results after the tenths round. Therefore, 20 sets of SSMs are built for each subject whereby each set is composed of 40 SSMs.

For comparison in the experiment, 20 sets of supervised SSMs (40 in each set) are built for each subject based on the 20 sets of randomly sorted and segmented EEG as described above. In particular, the i-th supervised SSM in each set is built by learning from the first i segments of the subject EEG together with the corresponding labels. The adapted SSMs in the example embodiments and the supervised SSMs for comparison are then used to classify other sessions of the subject EEG.

TABLE 1

|  | Subj. 1 | Subj. 2 | Subj. 3 | Subj. 4 | Subj. 5 | Subj. 6 | Subj. 7 | Subj. 8 | Subj. 9 | Subj. 10 |
| --- | --- | --- | --- | --- | --- | --- | --- | --- | --- | --- |
| Model 1 | 0.9878 | 0.8049 | 0.9268 | 0.8659 | 0.4146 | 0.8293 | 0.7195 | 0.6951 | 0.8537 | 0.4756 |
| Model 2 | 0.9024 | 0.9756 | 0.8293 | 0.5854 | 0.2927 | 0.4756 | 0.3659 | 0.4024 | 0.8415 | 0.4268 |
| Model 3 | 0.9146 | 0.7317 | 0.9878 | 0.8537 | 0.2561 | 0.8415 | 0.6341 | 0.7073 | 0.6829 | 0.6341 |
| Model 4 | 0.7805 | 0.4634 | 0.7683 | 1.0000 | 0.4024 | 0.8902 | 0.5976 | 0.4878 | 0.8780 | 0.3659 |
| Model 5 | 0.4878 | 0.2805 | 0.5000 | 0.6341 | 0.9024 | 0.6829 | 0.5244 | 0.6707 | 0.4024 | 0.1707 |
| Model 6 | 0.5854 | 0.1463 | 0.6585 | 0.8659 | 0.4024 | 1.0000 | 0.9512 | 0.9634 | 0.6829 | 0.1951 |
| Model 7 | 0.5488 | 0.2805 | 0.6585 | 0.8780 | 0.3659 | 0.8537 | 1.0000 | 0.8780 | 0.6585 | 0.2317 |
| Model 8 | 0.2439 | 0.2073 | 0.4390 | 0.5000 | 0.1098 | 0.8902 | 0.6585 | 1.0000 | 0.2073 | 0.3049 |
| Model 9 | 0.8902 | 0.8902 | 0.9024 | 0.9878 | 0.5366 | 0.9268 | 0.8293 | 0.8171 | 1.0000 | 0.5244 |
| Model 10 | 0.8415 | 0.6220 | 0.7195 | 0.5244 | 0.1463 | 0.5366 | 0.6220 | 0.7805 | 0.5610 | 0.9512 |

It should be noted that the use of 3 characters in the first segment as described above is preferable as it can improve the robustness of the technique in the example embodiments greatly. This is because if only a single character is included in the first segment and most of the EEG used to input that single character is incidentally misclassified by the SIM, the initially adapted SSM may not be able to capture the subject-specific P300 characteristics and the adaptation may not result in a good SSM eventually.

Figure 5:
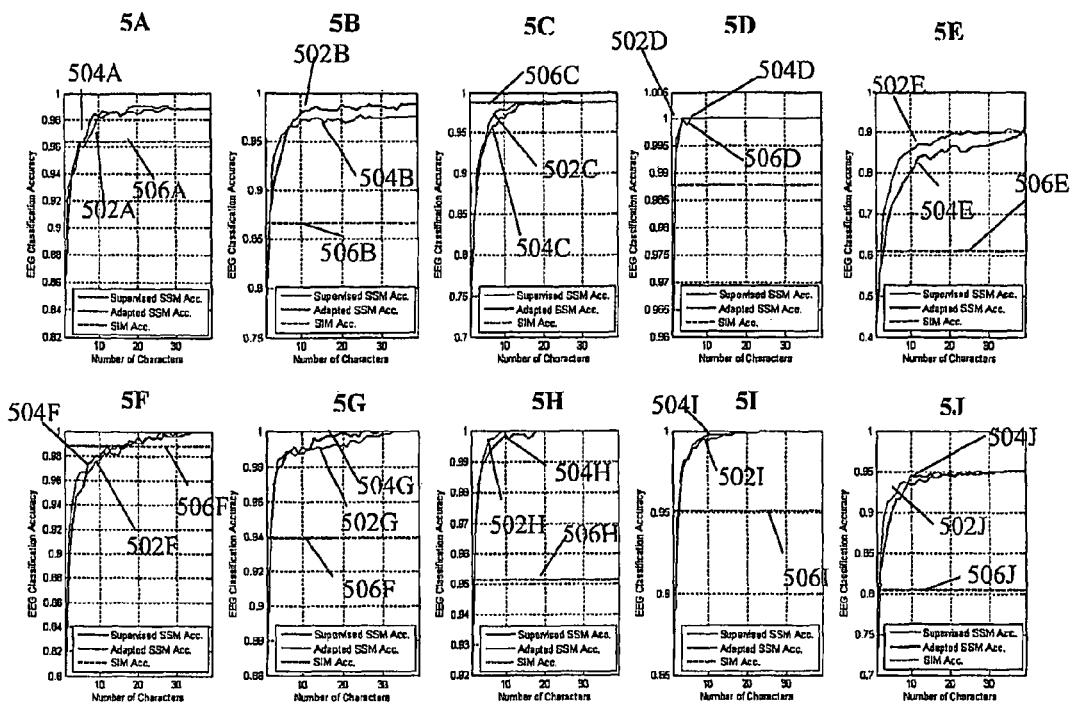
FIGS. 5A-J show graphs illustrating the accuracy of different P300 identification techniques.

FIGS. 5A-5J show graphs illustrating the P300 identification accuracy of supervised SSMs, the SIMs according to an example embodiment, and the adapted SSMs according to another embodiment of the present invention. In FIGS. 5A-J, the results for the ten healthy subjects averaged over the 20 sets of subject models are shown. In particular, the solid graphs 502A, 502B, 502C, 502D, 502E, 502F, 502G, 502H, 502I and 502J show the accuracy of the supervised SSMs whereas the dotted graphs 504A, 504B, 504C, 504D, 504E, 504F, 504G, 504H, 504I and 504J show the accuracy of the adapted SSMs in the example embodiment. As can be see from FIG. 5, while the accuracy of the adapted SSMs in the example embodiment is initially lower than that of the supervised SSMs for most of the subjects, the accuracy increases steadily and quickly converges to the accuracy of the supervised SSMs when around 25 characters are incorporated. In addition, even for the fifth subject whose EEG is quite different from the others as depicted in FIG. 5E, the accuracy of the adapted SSM in the example embodiment can also converge to the accuracy of the supervised SSM.

The accuracy in FIG. 5 is evaluated when ten rounds of test EEG data are used for each character. It is noted that the model accuracy is improved when more and more training data is used for supervised SSMs or adapted SSMs. For the SIMs, the accuracy does not change because the SIM is fixed (trained by the pooled EEG). The axis of the figures in FIG. 5 labelled "Number of characters" refers to the amount of training EEG data used for the training of the supervised and adapted SSMs, where each character corresponds to ten rounds of EEG that are used to spell the character. As described above for the test data, the training EEG data is likewise divided into 40 segments including 2 characters corresponding to 2*10 rounds of EEG in the first and 1 character in each thereafter in the example embodiment.

FIGS. 6A-J show graphs illustrating the standard deviation of the P300 identification accuracy of the supervised SSMs, and the adapted SSMs according to an embodiment of the present invention. For the ten healthy subjects, the graphs in FIG. 6 show the standard deviations of the model accuracy evaluated across the 20 sets of SSMs as described above. The solid graphs 602A, 602B, 602C, 602D, 602E, 602F, 602G, 602H, 602I and 602J show the standard deviation of the accuracy of the supervised SSMs whereas the dotted graphs 604A, 604B, 604C, 604D, 604E, 604F, 604G, 604H, 604I and 604J show the standard deviation of the accuracy of the adapted SSMs. As shown in FIG. 6, the standard deviation of the accuracy of the adapted SSMs is quite close to that of the supervised SSMs for most of the ten subjects (except for the fifth subject as depicted in FIG. 5E). At the same time, the accuracy variance of the adapted SSMs is quite small (except for the fifth subject as depicted in FIG. 5E), indicating the stability of the technique in this example embodiment. The fifth subject's much larger accuracy deviation may be because his P300 differs substantially from that of the other nine subjects.

Both the supervised and adapted SSMs are trained by increasing the number of the training characters step by step in this comparison. Particularly, the 41 training characters are divided into 40 segments (2 characters in the first segment and 1 in each of the remaining 39 segments) and train the SSMs (for both supervised and adapted) with the training character segments being increased from 1 to 40.

Figure 6:
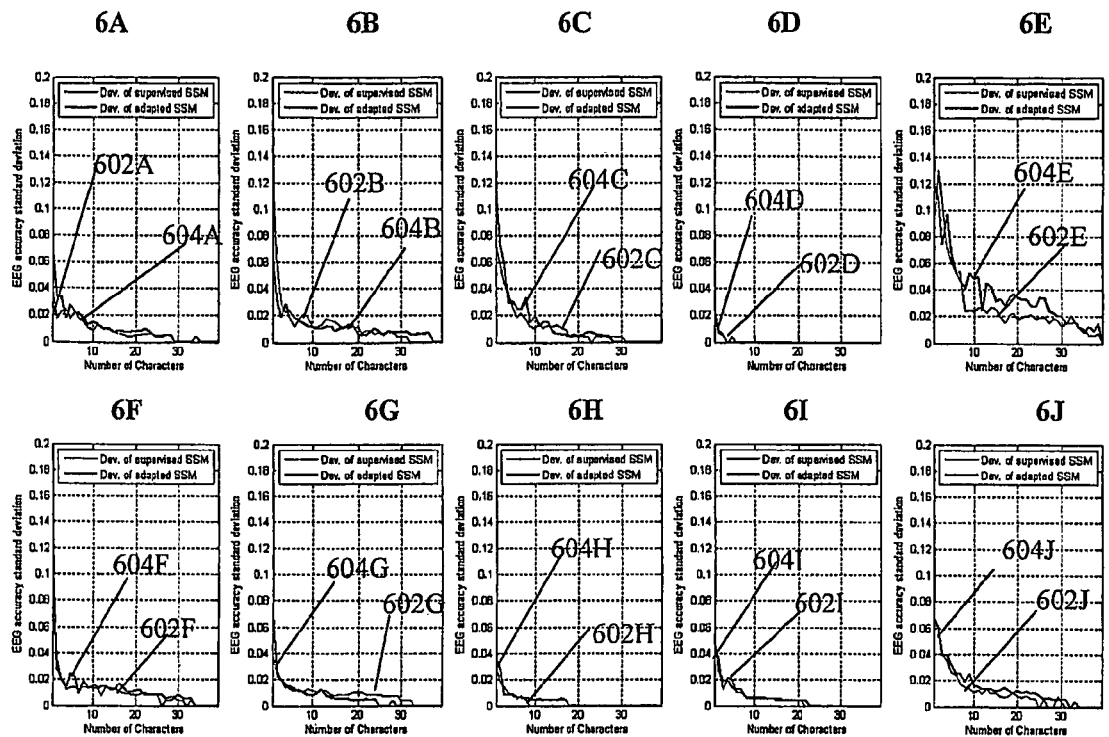
FIGS. 6A-J show graphs illustrating the standard deviation of the P300 identification accuracy of supervised SSMs and adapted SSMs according to an embodiment of the present invention.

The trained SSMs are then used to classify the test data (another EEG session composed of 41 characters) as illustrated in FIGS. 5 and 6. As can be seen from FIGS. 5 and 6, the SSM accuracy (evaluated over the test data) increases steadily when more EEG (from the training EEG) is used for the model training.

Figure 7:
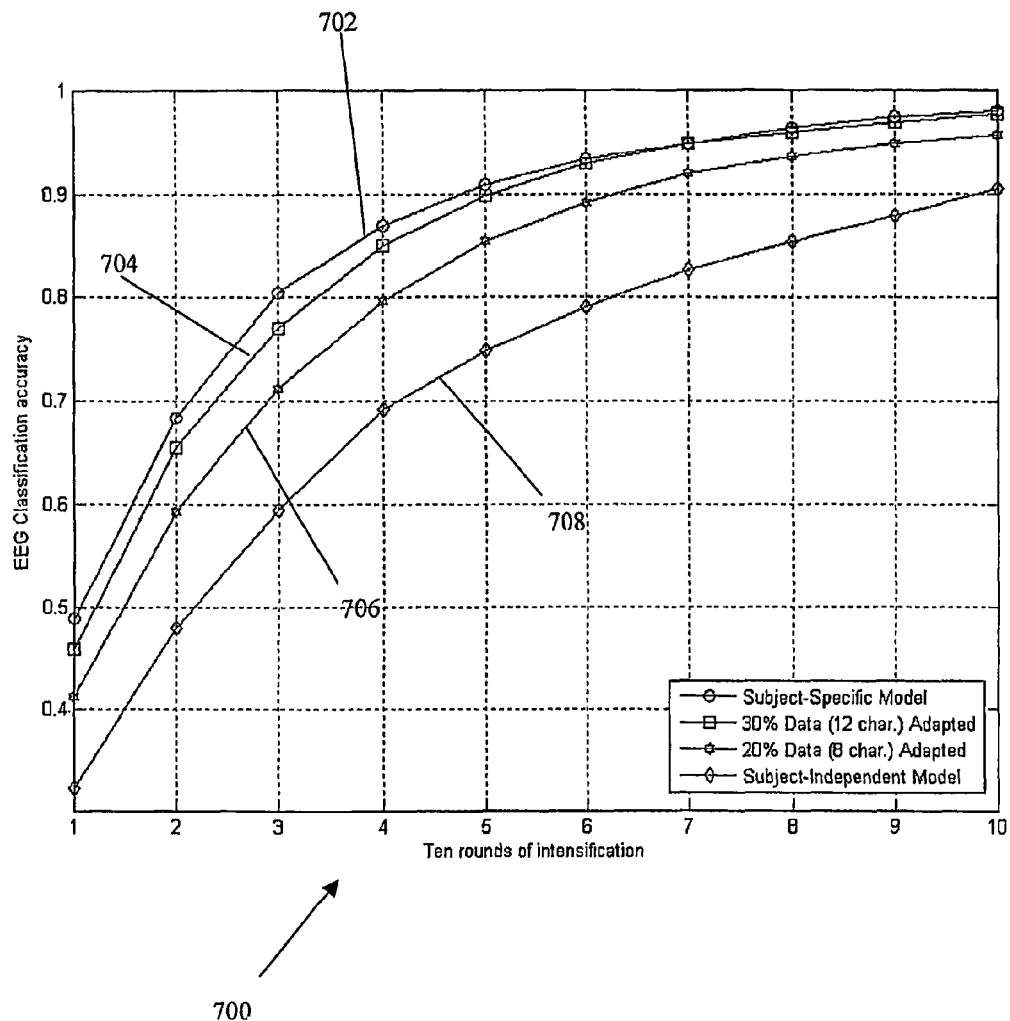
FIG. 7 shows a plot illustrating the classification accuracy of different P300 identification techniques.

FIG. 7 shows a plot 700 illustrating the classification accuracy of supervised SSMs, adapted SSMs according to an example embodiment, and SIMs according to another embodiment of the present invention over different rounds of intensification. In FIG. 7, graph 702 shows the classification accuracy of the supervised SSMs over different rounds of intensification, graphs 704 and 706 respectively show the classification accuracy of the adapted SSMs in the example embodiments when 20% of the data (8 characters) and 30% of the data (12 characters) are adapted and graph 708 shows the classification accuracy of the SIMs in the example embodiment over different rounds of intensification. As shown in FIG. 7, with a small amount of subject EEG incorporated during the SSM upgrading process, compared to supervised SSMs, the adapted SSM is capable of achieving virtually the same performance as the supervised SSM trained by labelled subject EEG.

It is noted that the accuracy of both SIMs and SSMs will increase when a larger number of rounds of EEG are used for the classification. Due to the noise, the single-round EEG classification accuracy is very low as illustrated in FIG. 7. To solve this problem, most existing BCIs collect EEG in multiple rounds and then suppress the noise effect through averaging the EEG collected in multiple rounds.

From the experimental results it can be seen that the SIM in an example embodiment outperforms the cross-subject model significantly. Furthermore, the SSM adapted with unlabelled subject EEG in another example embodiment not only outperforms the SIM but is also capable of achieving virtually the same performance as the supervised SSM trained by labelled subject EEG. This is achieved by using only a small amount of subject EEG incorporated during the SSM upgrading process, compared to the supervised SSM process. Compared with using the supervised SSMs, using the SIM and adapted SSMs in the example embodiments can remove the tedious and complicated training procedure. Therefore, P300-based BCIs can be made to be user-friendlier and more easily implemented.

Furthermore, the techniques in the example embodiments are not limited to identifying P300 using a P300-based word speller. The technique of learning a SIM from a pool of subjects and the adaptation of a SIM to a SSM in example embodiments can also be applied to other EEG-based BCIs such as those using motor imagery.

Hence, in one example embodiment, an adaptive EEG classification technique has been developed. In this technique in the example embodiment, a SIM is first built, which itself, as an embodiment of the invention, augments the classification of EEG of a new subject by learning from a pool of existing subjects. Next, the SIM is adapted to a SSM for a new subject through an unsupervised learning process. With application to a P300 word speller, experiments over ten healthy subjects show that the adapted SSM is capable of achieving virtually the same performance as the supervised SSM trained by labelled subject EEG. Hence, the use of the adapted SSM in this example embodiment can remove the complicated and tedious training process without compromising on its performance.

Figure 8:
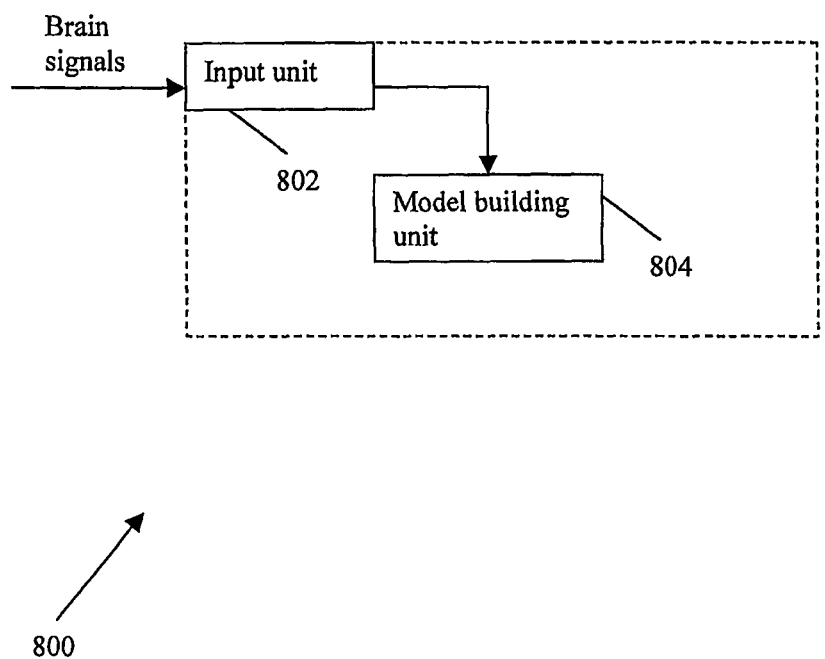
FIG. 8 illustrates a schematic block diagram of a system for classifying brain signals in a BCI according to an embodiment of the present invention.

FIG. 8 illustrates a schematic block diagram of a system 800 for classifying brain signals in the BCI according to an embodiment of the present invention. The system 800 includes an input unit 802 for receiving brain signals and a model building unit 804 for building a subject-independent model using labelled brain signals from a pool of subjects.

Figure 9:
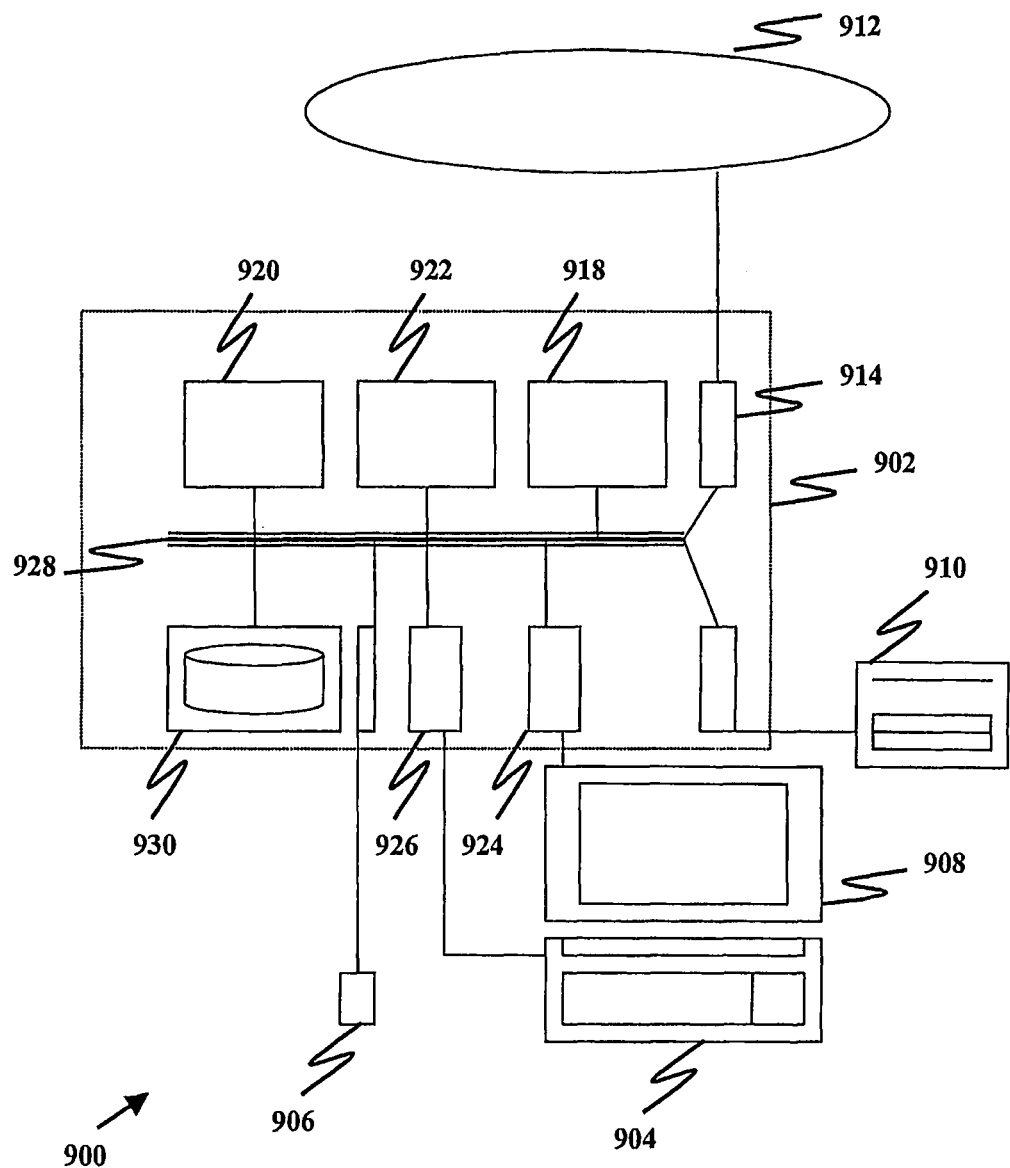
FIG. 9 illustrates a schematic block diagram of a computer system on which the method and system of the example embodiments can be implemented.

The method and system of the example embodiment can be implemented on a computer system 900, schematically shown in FIG. 9. It may be implemented as software, such as a computer program being executed within the computer system 900, and instructing the computer system 900 to conduct the method of the example embodiment.

The computer system 900 comprises a computer module 902, input modules such as a keyboard 904 and mouse 906 and a plurality of output devices such as a display 908, and printer 910.

The computer module 902 is connected to a computer network 912 via a suitable transceiver device 914, to enable access to e.g. the Internet or other network systems such as Local Area Network (LAN) or Wide Area Network (WAN).

The computer module 902 in the example includes a processor 918, a Random Access Memory (RAM) 920 and a Read Only Memory (ROM) 922. The computer module 902 also includes a number of Input/Output (I/O) interfaces, for example I/O interface 924 to the display 908, and I/O interface 926 to the keyboard 904.

The components of the computer module 902 typically communicate via an interconnected bus 928 and in a manner known to the person skilled in the relevant art.

The application program is typically supplied to the user of the computer system 900 encoded on a data storage medium such as a CD-ROM or flash memory carrier and read utilising a corresponding data storage medium drive of a data storage device 930. The application program is read and controlled in its execution by the processor 91B. Intermediate storage of program data maybe accomplished using RAM 920.

A method of classifying brain signals in a BCI according to an embodiment of the present invention comprises building a subject-independent model using labelled brain signals from a pool of subjects.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive. For example, while the use of EEG has been described in the example embodiments of the present invention, other types of brain signals such as MEG signals or a mixture of both MEG and EEG signals can also be used.

What is claimed is:

1. A method for classifying brain signals in a brain-computer interface (BCI), the method comprising the steps of:
   building a subject-independent model for a new subject using labelled brain signals from a pool of previous subjects, and
   building an initial subject-specific model for the new subject based on the subject-independent model and a segment of the unlabelled brain signals from the new subject.

2. The method as claimed in claim 1, wherein the step of building an initial subject-specific model is based on the subject-independent model and a set of feature vectors extracted from said segment of the unlabelled brain signals from the new subject, said segment being a first segment of the unlabelled brain signals, and the method further comprises applying both the subject-independent model and the initial subject-specific model for classifying subsequent segments of the unlabelled brain signals.

3. The method as claimed in claim 2, further comprising the step of adapting the initial subject-specific model using one or more of a group consisting of the subsequent segments of unlabelled brain signals from the new subject, the subject-independent model and the initial subject-specific model.

4. The method as claimed in claim 3, wherein the adapting is performed until the subject-specific model achieves a consistent confidence score and subsequently the adapted subject specific model is used to give the classification of the brain signals.

5. The method as claimed in claim 1, wherein the step of building the subject-independent model using labelled brain signals from a pool of previous subjects further comprises the steps of:
   acquiring the labelled brain signals from the pool of previous subjects;
   preprocessing the acquired labelled brain signals;
   constructing a set of feature vectors with their corresponding labels from the preprocessed brain signals; and
   building the subject-independent model by finding a weight vector for a linear combination of each feature vector to maximize the posterior probability that a P300 is evoked or not evoked given a feature vector.

6. The method as claimed in claim 2, wherein the step of building the initial subject-specific model comprises the steps of:
   acquiring the unlabelled brain signals from the new subject;
   segmenting the acquired unlabelled brain signals;
   preprocessing the acquired unlabelled brain signals;
   extracting a set of feature vectors from the preprocessed unlabelled brain signals; and
   classifying the first segment of the unlabelled brain signals using the subject-independent model to build the initial subject-specific model.

7. The method as claimed in claim 5, wherein the step of acquiring the labelled brain signals from the pool of previous subjects further comprises the steps of:
   providing a pre-defined set of stimuli in rows and columns;
   repeatedly activating the stimuli in rounds, wherein in each round, each row or column of stimuli is activated once;
   acquiring brain signals from the pool of previous subjects with each previous subject focused on a known stimulus; and
   labelling the acquired brain signals from the pool of previous subjects using the label of the known stimulus to give the labelled brain signals.

8. The method as claimed in claim 6, wherein the step of acquiring the unlabelled brain signals from the new subject further comprises the steps of:
   providing a pre-defined set of stimuli in rows and columns;
   repeatedly activating the stimuli in rounds, wherein in each round, each row or column of stimuli is activated once; and
   acquiring the unlabelled brain signals from the new subject with the subject focused on an unknown stimulus.

9. The method as claimed in claim 5, wherein the step of preprocessing the acquired labelled brain signals further comprises the steps of:
   implementing a low-pass filtering of the acquired labelled brain signals using an optimal cutoff frequency;

down-sampling the filtered brain signals by averaging every five consecutive samples to a single sample; and
removing ocular artifacts from the downsampled brain signals.

10. The method as claimed in claim 6, wherein the step of preprocessing the acquired unlabelled brain signals further comprises the steps of:
   implementing a low-pass filtering of the brain signals using an optimal cutoff frequency;
   down-sampling the filtered brain signals by averaging every five consecutive samples to a single sample; and
   removing ocular artifacts from the downsampled brain signals.

11. The method as claimed in claim 6 wherein the step of segmenting the acquired unlabelled brain signals further comprises the step of including brain signals collected for more than one stimulus in the first segment and including brain signals collected for one stimulus in each of the subsequent segments.

12. The method as claimed in claim 3, wherein the step of adapting the initial subject-specific model using one or more of a group consisting of the subsequent segments of unlabelled brain signals from the new subject, the subject-independent model and the initial subject-specific model further comprises the steps of iteratively:
   a) classifying the feature vectors corresponding to the subsequent segment of the unlabelled brain signals using the subject-independent model;
   b) classifying the feature vectors corresponding to the subsequent segment of the unlabelled brain signals using the initial subject-specific model;
   c) evaluating a confidence score for the subject-independent model;
   d) evaluating a confidence score for the initial subject-specific model;
   e) classifying the feature vector corresponding to the subsequent segment of the unlabelled brain signals using the model with a higher confidence score;
   f) determining if the initial subject-specific model has achieved a consistent confidence score;
   g) adapting the initial subject-specific model using classification results from the model with a higher confidence score if the subject-specific model has not achieved a consistent confidence score; and
   repeating steps a) to g) with the adapted initial subject-specific model as the initial subject-specific model.

13. The method as claimed in claim 12, wherein the step of evaluating the confidence score for the subject-independent model further comprises the steps of:
   evaluating a posterior probability that a P300 is evoked given the feature vector for each row of stimuli;
   evaluating a posterior probability that a P300 is evoked given the feature vector for each column of stimuli;
   determining the difference between the highest posterior probability among the rows of stimuli and the next highest posterior probability among the rows of stimuli to give a saliency of the highest posterior probability and multiplying said saliency to said difference;
   determining the difference between the highest posterior probability among the columns of stimuli and the next highest posterior probability among the columns of stimuli to give a saliency of the highest posterior probability and multiplying said saliency to said difference; and
   combining the product of the saliency and the difference for the rows of stimuli and the columns of stimuli to evaluate a confidence score for the subject-independent model.

14. The method as claimed in claim 12, wherein the step of evaluating the confidence score for the initial subject-specific model further comprises the steps of:
   evaluating a posterior probability that a P300 is evoked given the feature vector for each row of stimuli;
   evaluating a posterior probability that a P300 is evoked given the feature vector for each column of stimuli;
   determining the difference between the highest posterior probability among the rows of stimuli and the next highest posterior probability among the rows of stimuli to give a saliency of the highest posterior probability and multiplying said saliency to said difference;
   determining the difference between the highest posterior probability among the columns of stimuli and the next highest posterior probability among the columns of stimuli to give a saliency of the highest posterior probability and multiplying said saliency to said difference; and
   combining the product of the saliency and the difference for the rows of stimuli and the columns of stimuli to evaluate a confidence score for the initial subject-specific model.

15. The method as claimed in claim 12, wherein the step of determining if the initial subject-specific model has achieved a consistent confidence score further comprises the steps of:
   determining if the confidence score of the initial subject-specific model for a current segment of brain signals from the new subject is greater than a first threshold;
   determining if the standard deviation of the confidence scores of the initial subject-specific model for the last k segments of brain signals from the new subject is less than a second threshold; and
   determining that the initial subject-specific model has achieved a consistent confidence score if the confidence score of the initial subject-specific model for a current segment of brain signals is greater than said first threshold and the standard deviation of the confidence scores of the initial subject-specific model for the last k segments of brain signals is less than said second threshold.

16. The method as claimed in claim 8, further comprising the step of identifying the unknown stimulus by identifying the row and the column in which the unknown stimulus lies wherein the stimulus in said row and said column results in a maximum averaged posterior probability that P300 is evoked given a feature vector.

17. A system for classifying brain signals in a brain-computer interface (BCI), the system comprising:
   a first model building unit for building a subject-independent model for a new subject using labelled brain signals from a pool of previous subjects, and
   a second model building unit for building an initial subject-specific model for the new subject based on the subject-independent model and a segment of the unlabelled brain signals from the new subject.

18. The system as claimed in claim 17, wherein the second model building unit for building an initial subject-specific model is based on the subject-independent model and a set of feature vectors extracted from said segment of the unlabelled brain signals from the new subject, said segment being a first segment of the unlabelled brain signals, and the system is configured to apply both the subject-independent model and the initial subject-specific model for classifying subsequent segments of the unlabelled brain signals.

19. The system as claimed in claim 18, further comprising a model adapting unit for adapting the initial subject-specific model using one or more of a group consisting of the subsequent segments of unlabelled brain signals from the new subject, the subject-independent model and the initial subject-specific model.

20. The system as claimed in claim 19, wherein the adapting is performed until the subject-specific model achieves a consistent confidence score and subsequently the adapted subject specific model is used to give the classification of the brain signals.

21. The system as claimed in claim 17, further comprising:
a stimulation unit comprising a set of stimuli in rows and columns;
wherein the stimulation unit repeatedly activates the stimuli in rounds, such that in each round, each row or column of stimuli is activated once;
an acquisition unit for acquiring brain signals; and
a preprocessing unit for preprocessing the acquired brain signals.

22. A non-transitory data storage medium having stored thereon computer code means for instructing a computer system to execute a method for classifying brain signals in a brain-computer interface (BCI), the method comprising the steps of:
building a subject-independent model using labelled brain signals for a new subject from a pool of previous subjects, and
building an initial subject-specific model for the new subject based on the subject-independent model and a segment of the unlabelled brain signals from the new subject.

23. The non-transitory data storage medium as claimed in claim 22, wherein the step of building an initial subject-specific model is based on the subject-independent model and a set of feature vectors extracted from said segment of the unlabelled brain signals from the new subject, said segment being a first segment of the unlabelled brain signals, the method further comprises applying both the subject-independent model and the initial subject-specific model for classifying the subsequent segments of the unlabelled brain signals.

24. The non-transitory data storage medium as claimed in claim 23, the method further comprising the step of adapting the initial subject-specific model using one or more of a group consisting of the subsequent segments of unlabelled brain signals from the new subject, the subject-independent model and the initial subject-specific model.

25. The non-transitory data storage medium as claimed in claim 24, wherein the adapting is performed until the subject-specific model achieves a consistent confidence score and subsequently the adapted subject specific model is used to give the classification of the brain signals.

\* \* \* \* \*